(12) United States Patent
Guilhabert-Goya et al.

(10) Patent No.: US 8,623,813 B2
(45) Date of Patent: Jan. 7, 2014

(54) SYNERGISTIC COMBINATIONS OF POLYENE FUNGICIDES AND NON-RIBOSOMAL PEPTIDES AND RELATED METHODS OF USE

(75) Inventors: Magalie Guilhabert-Goya, Davis, CA (US); Jonathan S. Margolis, Davis, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 13/478,989

(22) Filed: May 23, 2012

(65) Prior Publication Data

US 2012/0302494 A1 Nov. 29, 2012

Related U.S. Application Data

(60) Provisional application No. 61/489,640, filed on May 24, 2011, provisional application No. 61/615,075, filed on Mar. 23, 2012.

(51) Int. Cl.
*A01N 37/18* (2006.01)

(52) U.S. Cl.
USPC ............................................ 514/3.3; 514/2.4

(58) Field of Classification Search
None
See application file for complete search history.

(56) References Cited

U.S. PATENT DOCUMENTS

| | | | |
|---|---|---|---|
| 5,895,680 | A | 4/1999 | Cirigliano et al. |
| 5,902,579 | A | 5/1999 | Eisenschink et al. |
| 6,060,051 | A | 5/2000 | Heins et al. |
| 6,291,426 | B1 | 9/2001 | Heins et al. |
| 6,638,910 | B2 | 10/2003 | Heins et al. |
| 2002/0031504 | A1* | 3/2002 | Beudeker ............... 424/94.1 |
| 2003/0026797 | A1 | 2/2003 | Beudeker |
| 2010/0305055 | A1 | 12/2010 | Bonvila et al. |
| 2011/0047654 | A1 | 2/2011 | Stark et al. |

FOREIGN PATENT DOCUMENTS

| | | |
|---|---|---|
| AU | 1989/39235 | 9/1990 |
| EP | 1949789 A1 | 7/2008 |
| FR | 2644038 | 4/1989 |
| FR | 2644038 A1 | 9/1990 |
| JP | 07118169 A * | 5/1995 |
| JP | 2915296 A | 5/2005 |
| WO | 03/013251 A1 | 2/2003 |
| WO | WO 03/013251 | 2/2003 |
| WO | 2006032646 A1 | 3/2006 |
| WO | WO 2009/037242 | 3/2009 |
| WO | WO 2010/033714 | 3/2010 |
| WO | WO 2010/108973 | 9/2010 |
| WO | WO 2010/128003 | 11/2010 |
| WO | WO 2010/139656 | 12/2010 |
| WO | WO 2011/116155 | 9/2011 |
| WO | WO 2012/087980 | 6/2012 |

OTHER PUBLICATIONS

Machine translation of JP 2915296, Translated by WWW4.IPDL. INPPIT.GO.JP, at http://www4.ipdl.inpitgo.jp/Tokujitu/tjsogodbenk.ipdl on Dec. 7, 2012.*

Loeffler et al., Antifungal Effects of Bacilysin and Fengymycin from *Bacillus subtilus* F-29-3 A Comparison with Activities of Other *Bacillus* Antibiotics, J. Phytopathology, vol. 115 p. 204-213 (1986).*

Freire et al, Chapter 23: Biosurfactants as Emerging Additives in Food Processing, Innovation in Food Engineering: New Techniques and Products, CRC Press (2009), pp. 685-705, attached as PDF, available online at http://www.crcnetbase.com/doi/abs/10.1201/9781420086072-c23.*

Norio, Kimura et al., Abstract of French Patent Number FR 2644038 filed Sep. 14, 1990 (printed from http://worldwide.espacenet.com/publication) on Nov. 7, 2012.

Invitation to Pay Additional Fees (Form PCT/ISA/206) for PCT/US2012/039178, mailed Oct. 1, 2012.

Maget-Dana, Regine, et al.," Iturins, a special class of pore-forming lipopeptides: biological and physicochemical properties," Toxicology, vol. 87, pp. 151-174, 1994.

Ibrahim, Ashraf S. et al.," Combination Therapy of Murine Mucormycosis or Aspergillosis with Iron Chelation, Polyenes, and Echinocandins," Antimicrobial Agents and Chemotherapy, vol. 55, (4):1768-1770, Apr. 2011.

Reed, Caitlin et al.," Combination Polyene-Caspofungin Treatment of Rhino-Orbital-Cerebral Mucormycosis," Clinical Infectious Disease, vol. 47, pp. 364-371, Aug. 2008.

Ongena, M., "*Bacillus* Lipopeptides: Versatile Weapons for Plant Disease Biocontrol,"Trends in Microbiology, 2008, pp. 115-125, vol. 16, No. 3.

International Search Report and Written Opinion of the International Searching Authority, International Patent Application No. PCT/US2012/039178, Feb. 12, 2013, 17 pages.

* cited by examiner

*Primary Examiner* — Cecilia J Tsang
*Assistant Examiner* — Randall L Beane
(74) *Attorney, Agent, or Firm* — Michelle L. Samonek

(57) ABSTRACT

The present invention includes compositions comprising a synergistic fungicidal combination of a polyene fungicide and at least one lipopeptide and methods for using such compositions in controlling fungal pathogens.

8 Claims, 9 Drawing Sheets

SYNERGISTIC COMBINATIONS OF POLYENE FUNGICIDES AND NON-RIBOSOMAL PEPTIDES AND RELATED METHODS OF USE

FIELD OF INVENTION

The present invention relates to synergistic combinations of polyene fungicides with antibiotic non-ribosomal peptides, such as amphiphilic cyclic lipopeptides, to improve the fungicidal activity of both components.

BACKGROUND OF INVENTION

Fungicides have myriad uses, including for crop protection; as food, feed, and cosmetics preservatives; and as pharmaceuticals for both human and veterinary applications. Crop yield reduction, food-borne diseases and fungal infections of both humans and animals are a problem in both developed and developing countries. Therefore, improvements to the efficacy of existing fungicides, especially those that are environmentally friendly and are not susceptible to development of fungal resistance are highly desirable.

Polyene fungicides are antifungal antibiotics that have been used in all of the aforementioned fields. They may be obtained through fermentation of *Streptomyces* species, such as *Streptomyces natalensis*, which is commonly found in soil. Activity of polyene fungicides derives, in part, from their ability to damage cell membranes by forming complexes with ergosterol. Numerous studies have confirmed that the potential for development of fungi resistant to natamycin is very low. Further, polyene fungicides have negligible toxicity, as they do not affect the cholesterol present in mammalian cells.

Non-ribosomal peptides, including cyclic amphiphilic lipopeptides such as surfactins, iturins and fengycins, are well-recognized for their antimicrobial properties and have been used in the field of crop protection. Because of their mode of action, they also have potential uses in biopharmaceutical and other biotechnology applications. Lipopeptides may be obtained through fermentation of various soil bacteria, including *Bacillus subtilis* and *Bacillus amyloliquefaciens*. Lipopeptides, similarly to polyene fungicides, kill fungi by disrupting cell membranes. The potential for the development of fungal resistance to these compounds is expected to be very low since they act directly upon membrane lipids and not on a single site protein target. Further, lipopeptides are environmentally friendly and of low risk to workers and consumers; in fact, crops treated with lipopeptide-containing *Bacillus* strains may be harvested on the day of treatment. Applicants have discovered that combinations of polyene fungicides and lipopeptides cause a synergistic, rather than simply an additive, increase in efficacy against microorganisms such as fungi. Without wishing to be bound by any theory, Applicants hypothesize that the lipopeptides and polyene fungicides of the present invention act in a synergistic fungicidal manner because each type of compound disrupts fungal cell membranes via a distinct mode of action.

SUMMARY OF INVENTION

The present invention provides a low-tox, low resistance-inducing, increased-efficacy fungicidal composition that comprises components that are less toxic than many traditional synthetic fungicides and that are applied at rates lower than either compound individually. This fungicidal composition is comprised of a synergistic fungicidal combination of one or more polyene fungicides and at least one lipopeptide.

In one embodiment, the polyene fungicide is one or more of natamycin, nystatin, amphotericin B, aureofungin, filipin and lucenosomycin and/or derivatives of each of these polyene fungicides. In another embodiment, the composition includes more than one polyene fungicide.

The lipopeptide component of this synergistic fungicidal combination may be part of a fermentation product produced by a lipopeptide-producing microorganism, may be a crude extract of such fungicidal fermentation product, or may be purified or semi-purified from such fermentation product. In other embodiments the lipopeptides are synthetic or semi-synthetic (i.e., a parent lipopeptide is obtained from a microorganism and is derivatized). In some embodiments, the lipopeptide-producing microorganism is a *Bacillus* species bacteria. In others it is a Streptomycete. In still others it is a *Paenibacillus* species bacteria.

In a particular instance, the lipopeptide-producing bacteria is *Bacillus subtilis, Bacillus amyloliquefaciens* or any other *Bacillus* species that produces one or more lipopeptides. In yet another instance, the lipopeptides produced by such *Bacillus* species are from one or more of the following families: surfactin-type compounds, iturin-type compounds and fengycin-type compounds. Some *Bacillus* species that produce lipopeptides are described in the Detailed Description of Invention (e.g., *amyloliquefaciens, cereus, thuringiensis, coagulans, pumilus, licheniformis*); others will be known to those of skill in the art. In a particular instance, the lipopeptide-producing bacteria is *Bacillus subtilis* QST713. In one embodiment, the composition is comprised of a polyene fungicide component and a lipopeptide-containing fermentation product. In one instance the lipopeptide-containing fermentation product is from a *Bacillus* species bacteria, such as those mentioned above.

In some embodiments the lipopeptide component of the compositions of the present invention is comprised of one more of the following compounds: surfactin-type compounds, fengycin-type compounds, iturin-type compounds and fusaricidins. Iturin-type compounds that are suitable for the present invention include one or more of the following compounds: bacillomycin D, bacillyomycin F, bacillomycin L, bacillomycin LC (also known as bacillopeptin), mycosubtilin, iturin A, iturin $A_L$, and iturin C (with the latter three compounds referred to herein, collectively, as iturins). Fengycin-type compounds that are suitable for the present invention are fengycin A, fengycin B, plipastatin A, plipastatin B, the plipastatins and agrastatins, as described in U.S. Pat. No. 6,291,426 (with the latter four listings referred to herein, collectively, as plipastatins). Surfactin-type compounds that are suitable for the present invention are esperin, lichenysin, pumilacidin and surfactin. In a particular embodiment, the lipopeptide component includes one or more of iturin-type compounds, such as iturin As, mycosubtilin and/or bacillomysin, fengycin-type compounds and surfactin. In yet another embodiment the lipopeptide component includes at least two of the following compounds: iturins, fengycin-type compounds and surfactins.

In some embodiments the synergistic fungicidal combination is comprised of a polyene fungicide and one or more lipopeptides. In another embodiment the synergistic fungicidal combination is comprised of a polyene fungicide and two or more lipopeptides. The lipopeptides may be one or more compounds from one or more of the following families of compounds: surfactin-type compounds, iturin-type compounds and/or fengycin-type compounds. In one instance, the lipopeptides are comprised of one or more iturins and/or one or more fengycin-type compounds and/or surfactin. In one embodiment, the polyene fungicide component of the composition is natamycin or nystatin and the lipopeptide component is comprised of iturins (A, B and/or C), bacillomycin, surfactin, fusaricidin, and/or fengycin-type compounds, either individually or in combination. In one particular instance, the lipopeptides are semi-purified or purified from a fermentation product of a lipopeptide-producing *Bacillus* species bacteria. In still another instance of this embodiment, the polyene fungicide is natamycin or a derivative thereof or nystatin or a derivative thereof.

The weight to weight ratio of the polyene fungicide component of the composition to the lipopeptide component (e.g., a lipopeptide-containing fermentation broth, a crude extract containing lipopeptides; a purified or semi-purified lipopeptide extract; or chemically synthesized or derivatized pure lipopeptide(s)) is from about 500:1 to 1:500. In one embodiment, the weight to weight ratio of natamycin or a derivative thereof or nystatin or a derivative thereof to a lipopeptide component comprised of one or more compounds from one or more of the following families of compounds, surfactin-type compounds, iturin-type compounds, fengycin-type compounds, and/or fusaricidins is about 500:1 to about 1:500. In one particular embodiment the weight to weight ratio of natamycin or a derivative thereof or nystatin or a derivative thereof to a lipopeptide component that includes a combination of iturin-type compounds, surfactin-type compounds and/or fengycin-type compounds is about 500:1 to about 1:500. In some embodiments, the weight to weight ratio of natamycin or a derivative thereof or nystatin or a derivative thereof to a lipopeptide component containing one or more iturin-type compounds, such as iturin As and/or bacillomycin is about 500:1 to about 1:500; in others, the weight to weight ratio of natamycin or a derivative thereof or nystatin or a derivative thereof to a lipopeptide component containing fengycin-type compounds is about 500:1 to about 1:500; in still others the weight to weight ratio of natamycin or a derivative thereof or nystatin or a derivative thereof to a lipopeptide component containing surfactin-type compounds, such as surfactin, is about 500:1 to about 1:500. In one embodiment, the weight to weight ratio of natamycin or a derivative thereof or nystatin or a derivative thereof to a crude extract of lipopeptides from fermentation broth, including fermentation broth containing fengycin-type compounds, iturin-type compounds and/or surfactin-type compounds, is about 1:500 to about 500:1. In some embodiments the weight to weight ratio of any of the above-described combinations of polyene fungicide and a lipopeptide component is about 100:1 to about 1:100; in others it is about 10:1 to about 1:10; in still other it is about 5:1 to about 1:5; in yet others is it about 2:1 to about 1:2; and in yet others it is 1:1.

In one embodiment, the polyene fungicide component is natamycin or a derivative thereof or nystatin or a derivative thereof and the lipopeptide component includes one or more of the following: (i) iturin, (ii) bacillomycin, (iii) mycosubtilin, (iv) esperin, (v) lichenysin, (vi) pumilacidin, (vii) surfactin, (viii) fengycin A, (ix) fengycin B, (x) plipastatin A, (xi) plipastatin B, and/or (xii) agrastatin. In another instance of the aforementioned embodiment, surfactin is excluded from the composition. In yet another embodiment, the polyene fungicide component is natamycin or a derivative thereof or nystatin or a derivative thereof and the lipopeptide component includes one or more of the following: (i) iturin, (ii) surfactin, (iii) fengycin and/or (v) plipastatin. In another instance of this embodiment, the derivative of natamycin or nystatin has equal or better fungicidal activity compared to the parent compound.

Compositions of the present invention are useful in various fungal control applications. The above-described compositions may be used to control fungal phytopathogens, post-harvest fungal pathogens, fungal pathogens of food or feed and human fungal pathogens.

In one embodiment, any of the above-described compositions are used to control target pathogens such as *Fusarium* species, *Botryis* species, *Verticillium* species, *Rhizoctonia* species, *Trichoderma* species and *Pythium* species by applying the composition to plants, the area surrounding plants, or edible cultivated mushrooms, mushroom spawn or mushroom compost. In one embodiment, the polyene fungicide component of compositions of the present invention used to control such pathogens is natamycin or a derivative thereof. In another it is nystatin or a derivative thereof.

In another embodiment, compositions of the present invention are used to control post-harvest pathogens such as *Penicillium, Geotrichum, Aspergillus niger,* and *Colletotrichum* species. In one embodiment, the polyene fungicide component of compositions used to control such pathogens is natamycin or a derivative thereof. In another it is nystatin or a derivative thereof.

In yet another embodiment, compositions of the present invention are used to control fungal pathogens that occur in food or feed, such as *Penicillium* species, *Aspergillus* species and *Fusarium* species. In one embodiment, the polyene fungicide component of compositions used to control such pathogens is natamycin or a derivative thereof. In another it is nystatin or a derivative thereof. In yet another, the lipopeptide component is a purified extract of one or more lipopeptides.

In still another embodiment, the compositions of the present invention are used to treat or prevent a fungal infection in a subject by administering to the subject a composition comprising a polyene fungicide and at least one polypeptide. In one embodiment the fungal infection is caused by *Candida* and the polyene fungicide used in the composition is nystatin or a derivative thereof. In another the fungal infection is caused by *Candida* and the polyene fungicide used in the composition is natamycin or a derivative thereof. In another the fungal infection is caused by *Fusarium* or *Aspergillus* and may be a corneal infection. In such instance, the polyene fungicide component used in the composition is natamycin or a derivative thereof. In another instance where the composition is used to treat a corneal infection the polyene fungicide component is nystatin or a derivative thereof. In yet another instance the lipopeptide component of the composition is a purified extract of one or more lipopeptides.

The present invention also includes a method for producing a fungicidal composition by making a combination of one or more polyene fungicides with one or more lipopeptides, testing the combination for synergistic efficacy against target fungi and producing a fungicidal composition comprising the combination and a carrier. In one embodiment, the one or more lipopeptides are part of or are an extract of a fermentation product from a *Bacillus* species bacteria, such as those described above and in the Detailed Description of Invention. In another instance of this embodiment, prior to making the combination, a lipopeptide-producing bacteria is selected, such as a *Bacillus* species strain or *Paenibacillus* species strain, and a fermentation product containing lipopeptides is produced using this lipopeptide-producing bacteria, and such fermentation product or an extract thereof is used to make the combination. In one instance, such fermentation product would include one or more of the following lipopeptides: surfactin-type compounds, fengycin-type compounds, iturin-type compounds and/or fusaricidin. In a more particular instance, such fermentation product would include one or more of the following lipopeptides: surfactin, plipastatin, fengycin, iturin and/or bacillomycin. In another embodiment, each of the polyene fungicide component and the lipopeptide component would be screened for fungicidal activity against the target pathogen prior to making the combination and only the polyene fungicide and lipopeptide components with at least some fungicidal activity would be used to make the combination. In other embodiments, target fungi are phytopathogens, such as *Fusarium, Botrytis* and *Verticillium*; post-harvest pathogens, such as *Penicillium* and *Geotrichum*; fungal pathogens of food or feed, such as *Aspergillus, Fusarium* and *Penicillium*; and human fungal pathogens, such as *Candida, Apsergillus* and *Fusarium*. *Saccharomyces cerevisiae* may also be used as a target pathogen in the above method as a model for *Candida*. In one instance, the polyene fungicide component of the tested combination is natamycin or a derivative thereof or nystatin and a derivative thereof. In another instance, the tested lipopeptides are one or more of surfactin-type compounds, iturin-type compounds, fengycin-type compounds and/or fusaricidins.

DETAILED DESCRIPTION OF INVENTION

Figure 1:
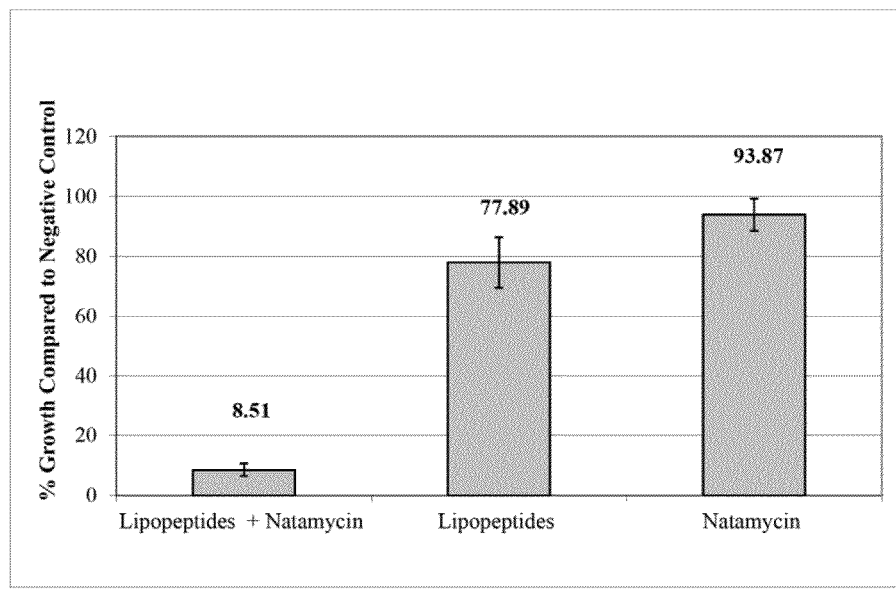
FIG. 1 shows percent growth of *Saccharomyces cerevisiae* compared to a negative control (receiving no treatment) in the presence of (i) crude extract of lipopeptides from *Bacillus subtilis* QST713 and natamycin, (ii) lipopeptides alone, or (iii) natamycin alone.

All publications, patents and patent applications, including any drawings and appendices therein, are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

The present invention encompasses synergistic combinations of polyene fungicides with antibiotic non-ribosomal peptides, other than enzymes, for control of microbial pathogens, such as fungi, oomycetes and/or bacteria.

Polyene fungicides of the present invention are antifungal antibiotics with a macrocyclic lactone ring having (i) a rigid lipophilic polyene portion and a flexible, hydrophilic hydroxylated portion and (ii) the ability to bind to a sterol in the cell membrane of most fungi, principally ergosterol. The macrocyclic lactone ring may have 12-40 carbons, 6-14 hydroxyl groups and may or may not be linked to a carbohydrate. The ring may be linked to one or more sugars such as a simple sugar with five or more carbon units, a deoxy sugar, amino sugars and the like, which contain substituent groups attached to the ring including oxygenated linkages. Polyene fungicides of the present invention may be obtained from a species of *Streptomyces* bacteria. Such fungicides include natamycin, nystatin, amphotericin B, aureofungin, filipin and lucensomycin as well as derivatives thereof. Examples of derivatives include the amphotericin B derivatives described in U.S. Pat. No. 5,606,038, for example, or the nystatin derivatives/analogues such as S44HP, NYST1068, and the octaene nystatin described in Bruheim et al., ANTIMICROBIAL AGENTS AND CHEMOTHERAPY, November 2004, pp. 4120-4129. Derivatives are naturally occurring analogs of a parent molecule or synthetic or semi-synthetic compounds derivatized from a parent molecule that retain at least some fungicidal activity compared to the parent molecule. In some embodiments, the derivatives have at least the same or greater fungicidal activity compared to the parent molecule. Derivatives include salts and solvates and other modified forms that have enhanced solubility compared to the parent molecule.

Antibiotic non-ribosomal peptides (NRPs) of the present invention are cell membrane or cell wall disrupting non-ribosomal peptides, excluding enzymes. Such antibiotic NRPs are synthesized by large enzymatic complexes called nonribosomal peptide synthetases, rather than by ribosomes. The term "antibiotic," as used herein, refers to the ability to kill or slow the growth of microbial pathogens, such as fungi, oomycetes and/or bacteria. A database of nonribosomal peptides called Norine is provided on the internet and described in Caboche, S., et al., "NORINE: A Database of Nonribosomal Peptides," *Nucleic Acids Research*, 36:D326-D331, (2008). Antibiotic NRPs of the present invention disrupt cell membranes, including organelle membranes, or cell walls. Membranes or walls may be disrupted through various means, including inhibition of synthesis of components of cell membranes or walls; physical disruption of the components of the cell membrane, such as through permeabilization of phospholipid membranes, either by membrane solubilization or osmotic perturbation; or binding to small molecules in the cell membrane.

Cell-wall disrupting antifungal NRPs of the present invention include echinocandins, which are semi-synthetic amphiphilic lipopeptides composed of a cyclic hexapeptide core linked to a variably configured lipid side chain. Echinocandins inhibit synthesis of 1,3-β-glucan, a predominant polysaccharide component of the ascomycete cell wall that maintains the osmotic integrity of the cell and is involved in cell division and growth. Echinocandins include caspofungin, micafungin and anidulafungin.

Cell-membrane disrupting antifungal NRPs of the present invention also include lipopeptides, such as amphiphilic cyclic peptides obtainable from various bacteria, including *Bacillus* sp., *Paenibacillus* sp., and *Streptomyces* sp. As used herein the term "lipopeptides" refers to amphiphilic cyclic peptides.

In some embodiments, these amphiphilic cyclic peptides are composed of six to ten α-amino acids linked to a β-amino or β-hydroxy fatty acid, such as the fengycin-type compounds, the iturin-type compounds, the surfactin-type compounds and the fusaricidins. The iturin-type compounds are composed of seven amino acids and are linked to a β-amino fatty acid. The length of the fatty acid chain may vary from C14 to C17. These compounds are obtainable from various species of *Bacillus*, including *subtilis* and *amyloliquefaciens*. The iturins and their variants are described in Ongena, M., et al., "*Bacillus* Lipopeptides: Versatile Weapons for Plant Disease Biocontrol," *Trends in Microbiology*, 16(3):115-125, (2007). Iturin-type compounds of the present invention include one or more of the following compounds: bacillomycin D, bacillyomycin F, bacillomycin L, bacillomycin LC (also known as bacillopeptin), mycosubtilin, iturin A, iturin $A_L$, and iturin C (with the latter three compounds referred to herein, collectively, as iturins).

Fengycin-type compounds are composed often amino acids linked to a β-hydroxy fatty acid with a chain that varies in length from C14 to C18. These compounds are obtainable from various species of *Bacillus*, including *subtilis, amyloliquefaciens, cereus* and *thuringiensis* and from *Streptomyces* sp. The fengycin-type compounds are described in Ongena, supra. Fengycin-type compounds suitable for the compositions described herein include fengycin A, fengycin B, plipastatin A, plipastatin B, the plipastatins from a *Streptomyces* sp. described in Kimura, et al., "SNA 60-367—New Peptide Enzyme Inhibitors against Aromatase," *Journal of Antibiotics*, 50(6): 529-531, (1997), and agrastatins, as described in U.S. Pat. No. 6,291,426 (with the latter four listings referred to herein, collectively, as plipastatins).

Surfactin-type compounds are composed of seven amino acids linked to a β-hydroxy fatty acid with a chain that varies in length from C13 to C16. These compounds are obtainable from various species of *Bacillus*, including *subtilis, amyloliquefaciens, coagulans, pumilus* and *licheniformis*. The surfactin family of compounds is described in Ongena, supra. Surfactin-type compounds of the present invention include one or more of the following compounds: esperin, lichenysin, pumilacidin and surfactin.

Fusaricidins are composed of six amino acids linked to a 15-guanidino-3-hydroxypentadecanoic acid. Fusaricidins are obtainable from *Paenibacillus* sp., including *polymyxa*. The fusaricidin family of compounds is described in Choi, S-K, et al., "Identification and Functional Analysis of the Fusaricidin Biosynthetic Gene of *Paenibacillus polymyxa* E681," *Biochemical and Biophysical Research Communications*, 365:89-95, (2008). Fusaricidins of the present invention include one or more of the following compounds: fusaricidins A-D and fusaricidins LI-F03, LI-F04, LI-F05, LI-F06, LI-F07 and LI-F08.

Certain bacteria produce one or more lipopeptides, and combinations of various lipopeptides are known to have synergistic fungicidal activity. In one embodiment, the lipopeptide component of the composition contains a combination of lipopeptides from at least two of the following lipopeptide classes: surfactin-type compounds, iturin-type compounds, and fengycin-type compounds. In another embodiment, the combination contains two or more of the following compounds: iturin As, plipastatins A and B, fengycins A and B and surfactin. In yet another embodiment, the combination contains one or more of the following compounds: iturin As, plipastatins A and B, fengycins A and B, surfactin and agrastatin.

Lipopeptides of the present invention are produced by one or more bacteria, such as those described above, or are chemically synthesized. The term "fermentation broth," as used herein, refers to the culture medium resulting after fermentation of a microorganism and encompasses the microorganism and its component parts, unused raw substrates, and metabolites produced by the microorganism during fermentation, among other things. The term "fermentation solid," as used herein, refers to concentrated and/or dried fermentation broth. The term "fermentation product," as used herein, refers to fermentation broth and/or fermentation solids. The term "lipopeptides," as used herein, refers to lipopeptides that are part of a fermentation product and to lipopeptides that are purified to at least some extent, whether chemically synthesized or biologically produced.

Methods of culturing bacteria are well known in the art. Conventional large-scale microbial culture processes include submerged fermentation, solid state fermentation, or liquid surface culture. For *Bacillus*, towards the end of fermentation, as nutrients are depleted, cells begin the transition from growth phase to sporulation phase, such that the final product of fermentation is largely spores, metabolites and residual fermentation medium. Sporulation is part of the natural life cycle of many *Bacilli* and is generally initiated by the cell in response to nutrient limitation. For this invention, fermentation is configured to obtain high levels of lipopeptides and to promote sporulation.

The bacterial cells, spores and metabolites in culture media resulting from fermentation (i.e., fermentation broth) may be used directly or concentrated (to make a fermentation solid) by conventional industrial methods, such as centrifugation, tangential-flow filtration, depth filtration, and evaporation. In some embodiments, the concentrated fermentation solid is washed, for example, via a diafiltration process, to remove residual fermentation broth and metabolites.

The fermentation broth or fermentation solids can be dried with or without the addition of carriers using conventional drying processes or methods such as spray drying, freeze drying, tray drying, fluidized-bed drying, drum drying, or evaporation. The resulting dry fermentation solids may be further processed, such as by milling or granulation, to achieve a specific particle size or physical format. Carriers, described below, may also be added post-drying, as appropriate for the desired method of use.

Bacterially produced lipopeptides may be separated from bacterial cells or further purified from other bacterial components and, in some embodiments, from each other. The term "cell-free preparation" refers to fermentation broth from which cells have been removed or substantially removed through means well known to those of skill in the art. Some methods of creating cell-free preparations are described below. Cell-free preparations of fermentation broth can be obtained by any means known in the art, such as extraction, centrifugation and/or filtration of fermentation broth. Those of skill in the art will appreciate that so-called cell-free preparations may not be devoid of cells but rather are largely cell-free or substantially cell-free, depending on the technique used (e.g., speed of centrifugation) to remove the cells. The resulting cell-free preparation may be dried and/or formulated with components that aid in its particular application. Concentration methods and drying techniques described above for fermentation broth are also applicable to cell-free preparations.

In some embodiments, after a cell-free preparation is made by centrifugation of fermentation broth, the metabolites may be purified by size exclusion filtration such as the Sephadex resins including LH-20, G10, and G15 and G25 that group metabolites into different fractions based on molecular weight cut-off, such as molecular weight of less than about 2000 daltons, less than about 1500 daltons, less than about 1000 daltons and so on, as the lipopeptides are between 800 daltons and 1600 daltons.

The term "crude extract," as used herein, refers to organic extracts of fermentation broth, such as ethyl acetate extracts, in which the extract is enriched for lipopeptides. One method to obtain a crude extract of lipopeptides from a bacterial culture is described in Example 1.

The term "semi-purified," as used herein, refers to lipopeptides isolated from fermentation broth that are about 50% to about 90% pure. The term "purified," as used herein, refers to lipopeptides that are isolated from fermentation broth that are about 91% to about 100% pure. Lipopeptides of the present invention may be either purified or semi-purified.

In one embodiment, lipopeptides of the present invention are obtained from *Bacillus subtilis* QST713 or a fermentation product of *Bacillus subtilis* QST713 is used as the lipopeptide-containing component of the composition. *Bacillus subtilis* QST713, its mutants, its supernatants, and its lipopeptide metabolites, and methods for their use to control plant pathogens and insects are fully described in U.S. Pat. Nos. 6,060,051; 6,103,228; 6,291,426; 6,417,163 and 6,638,910. In these patents, the strain is referred to as AQ713. *Bacillus subtilis* QST713 has been deposited with the NRRL on May 7, 1997, under the provisions of the Budapest Treaty on the International Recognition of the Deposit of Microorganisms for the Purpose of Patent Procedure under Accession Number B21661. Any references in this specification to QST713 refer to *Bacillus subtilis* QST713. Particular variants of *Bacillus subtilis* QST713 (e.g., *Bacillus subtilis* AQ30002 and AQ30004, deposited as Accession Numbers NRRL B-50421 and NRRL B-50455) that would also be suitable for the present invention are described in U.S. patent application Ser. No. 13/330,576.

In other embodiments, other *Bacillus* strains capable of producing lipopeptides are used as a source of lipopeptides for the present invention. As described above, fermentation broth or extracts from fermentation broth may be used as the lipopeptide-containing component of the synergistic fungicidal combination of the present invention. Methods for obtaining lipopeptides from a fermentation broth of QST713 are described in the examples. Obtaining lipopeptides from fermentation broth of *Bacillus* bacteria, in general, and analyzing fermentation broths for presence of lipopeptides is well known to those of skill in the art, such that other bacterial strains suitable for the present invention could be readily identified by the skilled artisan. *Bacillus* strains that produce various lipopeptides are described in the Ongena review article (*Trends in Microbiology* (2007) Vol. 16, No. 3) cited above. Myriad other articles describe lipopeptide-producing *Bacillus* strains and methods for extracting lipopeptides from fermentation broths of such strains: see; e.g., Alvarez, F., et al. "The plant-associated *Bacillus amyloliquefaciens* strains $MEP_218$ and $ARP_23$ capable of producing the cyclic lipopeptides iturin or surfactin and fengycin are effective in biocontrol of *sclerotinia* stem rot disease" *Journal of Applied Microbiology* (2011) 112: 159-174; Ongena, M. et al., "Involvement of fengycin-type lipopeptides in the multifaceted biocontrol potential of *Bacillus subtilis*," *Applied Microbiology Biotechnology* (2005) 69: 29-38; Wang, Y., et al., "Separation and extraction of antimicrobial lipopeptides produced by *Bacillus amyloliquefaciens* ES-2 with macroporous resin" *Eur. Food Res. Technol.* (2010) 23: 189-196.

Compositions of the present invention may include carriers, which are inert formulation ingredients added to compositions comprising a lipopeptide-containing fermentation product, cell-free preparations of lipopeptides or purified, semi-purified or crude extracts of lipopeptides to improve recovery, efficacy, or physical properties and/or to aid in packaging and administration. Such carriers may be added individually or in combination.

The compositions of the present invention may be used for various purposes, including protection of crops and of post-harvest fruits, vegetables and plants; as preservatives for cosmetics, processed foods, animal feed, or timber; and for pharmaceutical and veterinary applications. Depending on the particular application, the compositions will be formulated with appropriate carriers to aid in their application or administration. In some embodiments, the carriers are anti-caking agents, anti-oxidation agents, bulking agents, and/or protectants. Examples of useful carriers include polysaccharides (starches, maltodextrins, methylcelluloses, proteins, such as whey protein, peptides, gums), sugars (lactose, trehalose, sucrose), lipids (lecithin, vegetable oils, mineral oils), salts (sodium chloride, calcium carbonate, sodium citrate), silicates (clays, amorphous silica, fumed/precipitated silicas, silicate salts), waxes, oils, alcohol and surfactants.

Suitable carriers for animal feed additives are set forth in the American Feed Control Officials, Inc.'s Official Publication, which publishes annually. See, for example Official Publication of American Feed Control Officials, Sharon Krebs, editor, 2006 edition, ISBN 1-878341-18-9.

Compositions used for pharmaceutical or veterinary applications are combined with pharmaceutically acceptable carriers that vary based on the mode of administration.

Compositions of the present invention may be applied to a locus in need of treatment in an amount effective to control a pathogen. The term "control," as used herein, means to kill or inhibit the growth of the pathogen. In one embodiment the pathogen is a fungus. In another the pathogen is an oomycete.

In one embodiment, the polyene fungicide and the lipopeptide-containing component (e.g. purified or semi-purified lipopeptides, crude extracts, fermentation products or chemically synthesized or derivatized products) are applied at a 1:1 ratio (w/w). In another, the polyene fungicide to lipopeptide-containing component ratio is about 2:1, about 3:1, about 4:1, about 5:1, about 10:1, about 15:1, about 20:1, or about 50:1. In another, the polyene fungicide to lipopeptide-containing component ratio is about 1:2, about 1:3, about 1:4, about 1:5, about 1:10, about 1:15, about 1:20, or about 1:50.

In a specific embodiment, the polyene fungicide and a lipopeptide-containing component including one or more lipopeptides may be provided at various weight to weight (w/w) ratios in the composition. In one embodiment, the weight to weight ratio of the polyene fungicide and the lipopeptide-containing component is from about 500:1 to about 1:500. In another embodiment, the weight to weight ratio of the polyene fungicide and the lipopeptide-containing component is from about 100:1 to about 1:100. In another embodiment, the weight to weight ratio of the polyene fungicide and the lipopeptide-containing component is from about 10:1 to about 1:10. In another embodiment, the weight to weight ratio of the polyene fungicide and the lipopeptide-containing component is from about 5:1 to about 1:5. In another embodiment, the weight to weight ratio of the polyene fungicide and the lipopeptide-containing component is from about 2:1 to about 1:2. In another embodiment, the weight to weight ratio of the polyene fungicide and the lipopeptide-containing component is about 1:1.

In one embodiment, the composition is applied to a plant or to an edible cultivated mushroom. In plant applications, compositions may be applied to any part of a plant, including its root, foliage, or fruit, or to the area surrounding the plant, including the soil surrounding the plant. In mushroom applications, compositions may be applied to mushroom or to mushroom spawn or to mushroom compost. Application may occur before, at and/or post-planting. Exemplary target pathogens are *Fusarium* sp., *Botrytis* sp., *Verticillium* sp., *Rhizoctonia* sp., *Trichoderma* sp. (green mold), *Pythium* sp. and *Phytophthora* sp. Determining application rates for the present compositions is well known to those of skill in the art. A composition of the present invention will generally constitute 0.005 g/L to 100 g/L each of the polyene fungicide and the non-ribosomal protein(s), such as a lipopeptide. In one embodiment in which the synergistic composition is applied to a plant, plant part or to the area surrounding the plant or to an edible cultivated mushroom, mushroom spawn or mushroom compost, the polyene fungicide component is natamycin or a derivative thereof.

In another embodiment the locus is post-harvest food and post-harvest non-edible plant materials, such as feedstock for biofuel. Post-harvest food, as used herein, refers to fruit, vegetables, grains, oilseeds, and any other edible plants and nuts after harvest from the field but before packaging. Exemplary post-harvest pathogens include, but are not limited to: *Botrytis cinerea* (gray mold), pathogenic *Colletotrichum* species such as *Colletotrichum acutatum, Colletotrichumn coccodes, Colleotrichum musa*, and *Colletotrichum capsici, Erwinia carotovora* subsp. *carotovora, Geotrichum candidum, Geotrichum citri-aurantii* (sour rot), *Helminthosporium solani* (silver scurf of potato), *Monilinia fructicola* (brown rot), *Penicillium* sp., including *digitatum* (green mold of citrus) and *expansum* (blue mold of pome fruits), *Rhizopus* sp. (Rhizopus rot or leak), *Aspergillus niger* (black mold), *Thielaviopsis basicola* (black root rot of carrot), *mucor* rot of fruit (e.g., *Mucor piriformis* on pear), and *Alternaria* rots (mostly affecting carrots, broccoli, potatoes, peppers, apples, kiwis, pears, quinces and tomatoes). Determining application rates for the present compositions for post-harvest food and post-harvest non-edible plant materials is well known to those of skill in the art. In one embodiment where the composition is applied to post-harvest food and post-harvest non-edible plant materials, such as feedstock for biofuel, the polyene fungicide component is natamycin or a derivative thereof.

In yet another embodiment the locus is food or feed. The term food, as used herein includes processed foods, such as dairy products, breads, tortillas, deli meats, and bakery products; semi-processed or minimally processed foods, such as meat and cut fruit and vegetables; and packaged foods, such as packaged lettuce, spinach and other vegetables. The term feed includes processed animal feedstuffs and silage. In such applications the target pathogens are spoilage-inducing and mycotoxin-producing pathogens. Exemplary pathogens are *Aspergillus* sp., *Penicillium* sp. and *Fusarium* sp. Determining application rates for the present compositions is well known to those of skill in the art. Dose levels and recommended methods of application are described in detail in numerous references, including Davidson, P. Michael, et al., eds., Antimicrobials in Food, $3^{rd}$ ed. CRC Press 2005, Ch. 8, pp. 275-289. In one embodiment in which the synergistic composition of the present invention is applied to food or feed, the polyene fungicide component is natamycin or a derivative thereof.

In another embodiment the locus is a human or animal. In human and veterinary applications, the compositions are applied topically to the skin and mucosal membranes to control *Candida albicans* and/or *Fusarium* sp. In one embodiment, the compositions are used to prevent or treat vaginal infections, especially those caused by *Candida albicans* but also those caused by *C. glabrata, C parapsilosis, C. guilliermondii*, and *C. tropicalis*. In one embodiment in which the synergistic composition is applied to treat *Candida* the polyene fungicide component is nystatin. In humans, the compositions of the present invention may also be applied to nails, scalp and skin to control dermatophytes, such as Trichophyton, Epidermophyton and Microsporum, which are responsible for a variety of disease manifestations that localize to keratinized structures of the body (skin, nail and hair). In humans, the compositions may be administered as lozenges, to treat oral candidiasis or orally to treat or prevent intestinal candidiasis. Compositions of the present invention may also be used to treat *Aspergillus* and *Fusarium* corneal infections. In one embodiment wherein the compositions are used to treat corneal infections, the polyene fungicide component of the composition is natamycin or a derivative thereof. Determining appropriate administration rates for the present compositions would be well within the knowledge of one of skill in the art.

In some embodiments a locus in need of treatment is identified before the compositions are applied or administered.

In one embodiment, the compositions may include one or more pharmaceutically acceptable carriers. The pharmaceutically acceptable carriers may vary depending on their suitability for various dosage forms. In one embodiment, the compositions may include one or more pharmaceutically acceptable carriers as a topical composition. Topical composition can be in the form of a cream, gel, oil, spray, powder, paste, clay or any other form, way or method known in the art for administering the composition to the skin or a subject whether human or animal. The acceptable carrier contained in the topical composition may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these substances.

In one embodiment, the compositions may include one or more pharmaceutically acceptable carriers as an oral composition. The oral dosage forms may be in the form of a solid powder, caplets, tablets, lozenges, pills, capsules, soft-gel or a liquid, and which may be administered alone or in suitable combination with other components. For example, the composition of the present invention may be administered in one or more caplets or lozenges as practical for ease of administration. In preparing the composition in oral dosage form, any of the usual media may be utilized. For liquid preparations (e.g., suspensions, elixirs, and solutions), media containing, for example water, oils, alcohols, flavoring agents, preservatives, coloring agents and the like may be used. Pharmaceutical acceptable carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage unit form, in which case solid carriers are employed. If desired, tablets may be sugar coated or enteric coated by standard techniques. All of these pharmaceutical carriers and formulations are well known to those of ordinary skill in the art. See, e.g., WADE & WALLER, HANDBOOK OF PHARMACEUTICAL EXCIPIENTS (2nd ed. 1994).

In a specific embodiment of the present invention may comprise compositions in the dosage form of a soft-gel. A soft-gel is a one-piece, sealed, soft gelatin shell that contains a solution, a suspension, or a semi-solid paste. Soft-gels are predominantly used to contain liquids wherein the active ingredients are present in the dissolved or suspended state. Soft-gels have been widely known and used for many years and for a variety of purposes. Because soft-gels have properties that are quite different from two-piece, hard shell capsules, the soft-gels are capable of retaining a liquid fill material. Soft-gels are often used to encapsulate consumable materials, including vitamins, dietary supplements, pharmaceuticals, and the like, in a liquid vehicle or carrier. Soft-gels are a unique dosage form that can provide distinct advantages over more traditional dosage forms such as tablets, hard-shell capsules, and liquids. These advantages include patient compliance and consumer preference, improved bioavailability, speed of product development in many cases, shortened manufacturing time, enhanced drug stability due to less exposure of the active ingredient to oxygen, excellent dose uniformity, and product differentiation.

In one embodiment, the compositions and methods of the present invention may have a pleasant or palatable flavor. Palatable flavors may be achieved by including sweetening agents and/or flavorants. Sweetening agents that may be included in the compositions of the present invention include, by way of example and without limitation, sucrose, fructose, high fructose corn syrup, dextrose, saccharin sodium, maltodextrin, aspartame, potassium acesulfame, neohesperidin dihydrochalcone, sucralose, monoammonium glycyrrhizinate, and others known to those of ordinary skill in the art.

Disintegrants also may be included in the compositions of the present invention in order to facilitate dissolution. Disintegrants, including permeabilising and wicking agents, are capable of drawing water or saliva up into the compositions which promotes dissolution from the inside as well as the outside of the compositions. Such disintegrants, permeabilising and/or wicking agents that may be used in the present invention include, by way of example and without limitation, starches, such as corn starch, potato starch, pre-gelatinized and modified starches thereof, cellulosic agents, such as Ac-di-sol, montmorrilonite clays, cross-linked PVP, sweeteners, bentonite, microcrystalline cellulose, croscarmellose sodium, alginates, sodium starch glycolate, gums, such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents, such as hydroxymethylcellulose, hydroxypropylcellulose and hydroxyopropyl methylcellulose.

In addition to those described above, any appropriate fillers and excipients may be utilized in preparing the compositions of the present invention so long as they are consistent with the objectives described herein. For example, binders are substances used to cause adhesion of powder particles in granulations. Such compounds appropriate for use in the present invention include, by way of example and without limitation, acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, polyethylene glycol and others known to those of ordinary skill in the art.

Diluents also may be included in the compositions of the present invention in order to enhance the granulation of the compositions. Diluents can include, by way of example and without limitation, microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycin, and their mixtures.

Lubricants are substances used in composition formulations that reduce friction during composition compression. Lubricants that may be used in the present invention include, by way of example and without limitation, stearic acid, calcium stearate, magnesium stearate, zinc stearate, talc, mineral and vegetable oils, benzoic acid, poly(ethylene glycol), glyceryl behenate, stearyl fumarate, and others known to those of ordinary skill in the art.

Glidants improve the flow of powder blends during manufacturing and minimize composition weight variation.

Glidants that may be used in the present invention include, by way of example and without limitation, silicon dioxide, colloidal or fumed silica, magnesium stearate, calcium stearate, stearic acid, cornstarch, talc and others known to those of ordinary skill in the art.

Colorants also may be included in the compositions of the present invention. As used herein, the term "colorant" includes compounds used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide, red and others known to those of ordinary skill in the art. Coloring agents also can include pigments, dyes, tints, titanium dioxide, natural coloring agents, such as grape skin extract, beet red powder, beta carotene, annato, carmine, turmeric, paprika and others known to those of ordinary skill in the art.

Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery.

The compositions can include a solubilizer to ensure good solubilization and/or dissolution of the active ingredients such as the fungicide and/or lipopeptide. A solubilizer can also be added to increase the solubility of the fungicide and/or lipopeptide and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example, to maximize the concentration of the drug, with excess solubilizer removed prior to providing the 1 composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The following examples are given for purely illustrative and non-limiting purposes of the present invention.

EXAMPLES

Example 1

Synergistic Effect of Lipopeptides and Natamycin Against *Saccharomyces cerevisiae*

A combination of lipopeptides and natamycin was tested for efficacy against *Saccharomyces cerevisiae*, which is generally recognized as a model organism for testing activity against fungi and which is closely related to *Candida*. See Smits, G J, et al., "Stress Tolerance in Fungi—To Kill a Spoilage Yeast," *Current Opin Biotechnol.*, 16(2): 225-30, (2005) and Castrillo, J I, et al., "Yeast as a Touchstone in Post-Genomic Research: Strategies for Integrative Analysis in Functional Genomics," *J Biochem Mol Biol.*, 37(1): 93-106, (2004).

The lipopeptides used were a complex mixture of iturin-type compounds, plipastatin-type compounds, and surfactins partially purified from the fermentation broth of *Bacillus subtilis* QST713. Seed flasks containing Luria Broth (LB) were inoculated with the QST713 strain, and these flasks were grown overnight at 30° C. The next day, aliquots from the seed flask were inoculated into a soy-based medium and grown until sporulation. The *B. subtilis* QST713 fermentation broth was acidified to pH 2 and centrifuged to separate the solid material from the supernatant. The lipopeptides concentrated in the pellet. The supernatant was decanted and the pellet was extracted with an aqueous organic solvent mixture (preferably 80/20 acetonitrile/water). The lipopeptides concentrated in the aqueous organic fraction. The mixture was centrifuged and the supernatant removed. The cell pellet was re-extracted two additional times with an aqueous organic solvent mixture (preferably 80/20 acetonitrile/water). The supernatants from each extraction were combined and the solvent removed en vacuo. The dried extract contained an enriched form of all three classes of lipopeptides found in *B. subtilis* QST713: iturin-type compounds, including iturin A2, iturin A3, A4, or A5, iturin A6, iturin A7; fengycin-type compounds, including pilpastatin A1, plipastatin A2, plipastatin B1, plipastatin B2, agrastatin A, agrastatin B, fengycin A, fengycin B; surfactin A1, A2, or A3, surfactin B1 or B2 and surfactin C1 or C2. The dried extract can be resuspended in an aqueous organic solvent mixture (preferably 80/20 acetonitrile/water).

*Saccharomyces cerevisiae* wild-type strain BY4742 was grown in liquid YPD in the presence of: (1) natamycin (Haorui Pharma-Chem Inc), (2) the above-described lipopeptide extract, (3) natamycin+lipopeptide extract, and 4) no lipopeptides or natamycin (control). The initial concentration of natamycin before being added to the liquid culture was 1 ppm and the initial concentration of lipopeptide extract was 15 ppm. Final concentration of natamycin in the liquid culture was 0.08 ppm and final concentration of lipopeptide extract was 1.12 ppm, such that the weight to weight ratio of natamycin to lipopeptide in the sample containing both was 1:14.

The optical densities (OD) of liquid cultures containing natamycin and/or lipopeptides were compared to those of control cultures after 16 hours of growth at 30° C. For comparison, the OD of the untreated control cultures was set at 100% and the treated cultures were normalized to this value.

Gowing's Equation was applied, as follows, to determine synergism of lipopeptides with natamycin.

Gowing's Equation: $E_{xp}=X+[Y^*(100-X)]/100$

If $E_{ob}>>E_{xp}$, then synergy exists

NOTE: $E_{ob}$, $E_{xp}$, X and Y in the above equation represent growth inhibition. Thus, X and Y are calculated by subtracting the amount of growth on a treated plate from 100, as shown below.

$X=100-77.89=22.11$, $Y=100-93.87=6.13$ $E_{ob}=100-8.51=91.49$ $E_{xp}=22.11+[6.13^*(100-22.11)]/100=26.88$ $E_{ob}>>E_{xp}$

Results are also shown in FIG. 1.

Example 2

Synergistic Effect of Natamycin and Lipopeptides Against *S. cerevisiae* Using Lipopeptides Obtained from Commercially Available Product This study, which is similar to that described in Example 1, is conducted using a crude extract of lipopeptides obtained from SERENADE® MAX fungicide or SERENADE® ASO fungicide as a starting point (rather than from unformulated fermentation broth of *Bacillus subtilis* QST713). The SERENADE® products are commercially available, and their active ingredient is *Bacillus subtilis* QST713. A crude extract of lipopeptides is obtained by acidifying SERENADE®ASO (or SERENADE® MAX, dissolved in water) to pH 2, centrifuging and extracting the resulting pellet with an organic solvent mixture. The resulting lipopeptides are combined with natamycin as described above and this mixture tested for activity against *S. cerevisiae*. The same results as obtained above are expected.

Example 3

Synergistic Effect of Natamycin and a Crude Extract of Lipopeptides Against *Penicillium expansum*

The effect of (i) natamycin (Haorui Pharma-Chem. Inc.), (ii) a crude extract of lipopeptides from *Bacillus subtilis* QST713 (prepared as described in Example 1), and (iii) a combination of natamycin and a crude extract of lipopeptides on *Penicillium expansum* was investigated. A liquid fungal growth assay was performed in 96-well plates to determine whether the combination of lipopeptides and natamycin is synergistic in inhibiting fungal growth. All procedures were conducted aseptically.

For each 96 well plate, three separate additions were made to each well. First, 100 μl of potato dextrose broth w/100 ppm chloramphenicol was added. Then 25 μl of each sample (lipopeptides, natamycin, or combo from dilution plate) was supplemented. Finally, 50 μl of DI $H_2O$ was added to the blank plate (the plate intended to be left blank for an OD reference) OR 50 μl of $10^5$ fungal inoculum was added to each well in its respective plate(s). Thus, the final concentration of lipopeptide in each well was 1.1 ppm and the final concentration of natamycin in each well was 1.1 ppm. The plates were then covered with lids and placed at 20° C. for 3 days of incubation.

Rating Plates and Interpreting Data

After the incubation period, the growth of each well in each plate was rated by optical density at 600 nm using a PerkinElmer Victor plate-reader using the setting "MIC Settings @600 (0.1 s)" that can be found in the Wallac® Victor® software. The results were also roughly assessed visually as cloudy wells (partial growth) appearing in the dilution series where the sample fell off in activity.

After an OD was obtained for each well, the relative growth was determined by the following calculation: [(Treatment w/Bacteria)−(Treatment w/o Bacteria)/(Diluent Control w/Bacteria)−(Diluent Control w/o Bacteria)]×100. The positive control wells for bacterial growth were considered acceptable if the average and standard deviation of the OD readings at 600 nm were well above the range of the non-inoculated OD reference wells. (There must be a large difference between the un-inoculated diluent control and the inoculated diluent control wells' readings to ensure that good growth was obtained).

This percent growth was then graphed against the sample for the dilutions tested and the last dilution providing at least 80% of growth inhibition was taken as the minimum inhibitory concentration (MIC).

Synergy was then determined by Gowing's Equation, set forth above.

In this example, the Percent Growth of 1.1 ppm Lipopeptides was 113%. The Percent Growth of 1.1 ppm Natamycin was 102%. The Percent Growth of 1.1 ppm Lipopeptide+1.1 ppm Natamycin was 20.4%.

$X=100-102.1$ $Y=100-112.9$

Exp=−2.1+(−12.9(102.1))/100

Exp=−15.3

Alternatively, for Percent Growth that is over 100, round down to 100. In our example, this would make Exp=0

Eob=100−20.4

Eob=79.6

79.6>>−15.3

Figure 2:
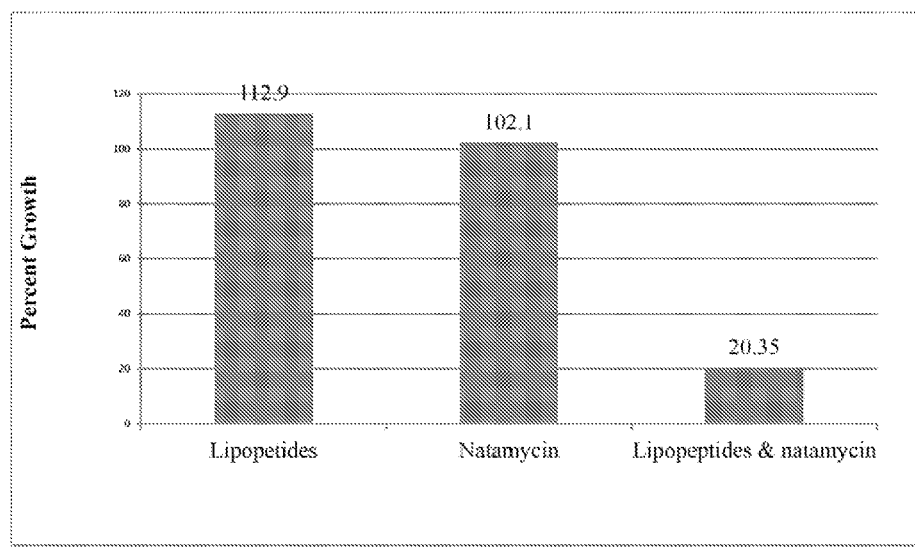
FIG. 2 shows percent growth of *Penicillium expansum* compared to a negative control in the presence of (i) a crude extract of lipopeptides, (ii) natamycin, and (iii) lipopeptides and natamycin.

Eob>>Exp; therefore, synergy is observed, as depicted in FIG. 2.

Example 4

Synergistic Effect of Semi-Purified and Purified Plipastatins, Iturins and Surfactins and Natamycin Against *Penicillium expansum*

Experiments similar to those described above, using *Penicillium expansum* as the target pathogen, were conducted with combinations of (i) natamycin and crude extracts of lipopeptides from *Bacillus subtilis* QST713 (obtained as described above) and (ii) natamycin and semi-purified and purified lipopeptides obtained from *Bacillus subtilis* QST713, as follows. Iturin-type compounds, including iturin As, and fengycin-type compounds, including plipastatins (A, B and agrastatins) and fengycins, were precipitated and extracted from *B. subtilis* QST713 fermentation broth using acidification followed by extraction with an organic solvent. These lipopeptides were further purified and separated through reversed-phase chromatography to obtain fengycin-type compounds that were about 83% pure and iturins that were about 88% pure. Surfactins were extracted using an organic solvent and then further purified using size exclusion column chromatography to 95% purity. Purity of each lipopeptide class was determined using a high performance liquid chromatography trace.

Final concentration of natamycin in each test well was 2.23 ppm; final concentration of the crude lipopeptide extract in each well was 2.23 ppm; final concentration of each semi-purified or purified lipopeptide extract of iturin-type compounds, surfactin or fengycin-type compounds in each well was 2.23 ppm. Thus, the weight to weight ratio of each component in the wells containing combinations was 1:1.

Figure 3:
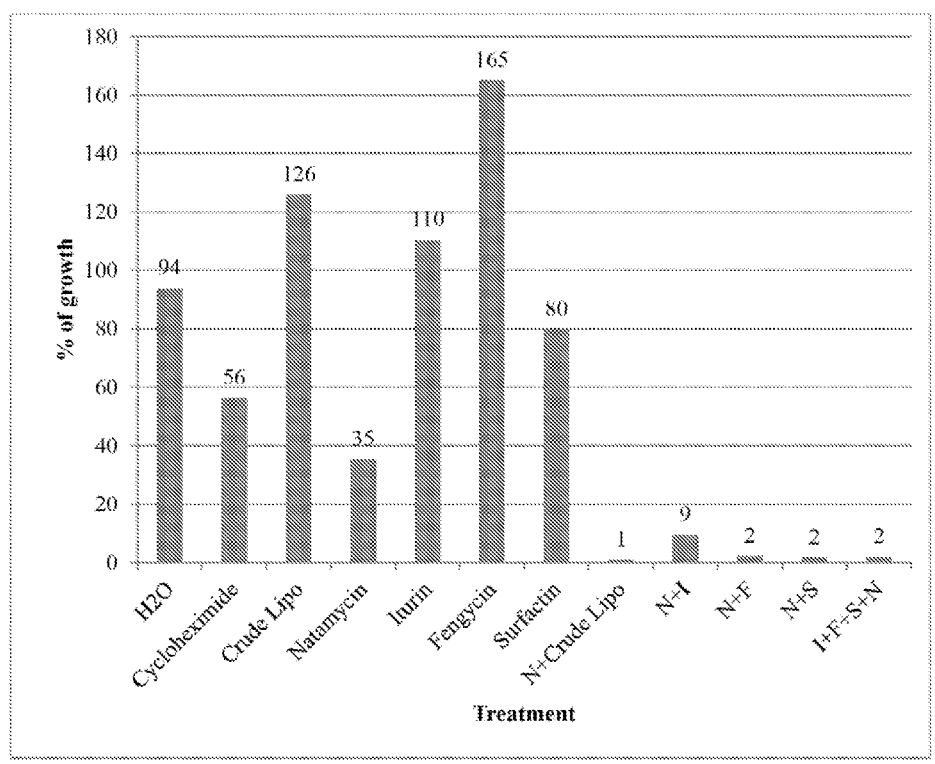
FIG. 3 shows percent growth of *Penicillium expansum* compared to a negative control in the presence of (i) natamycin, (ii) a crude lipopeptide extract, (iii) various semi-purified or purified lipopeptides (iv) combinations of natamycin and a crude lipopeptide extract and (v) combinations of natamycin and each semi-purified or purified lipopeptide or all semi-purified or purified lipopeptides. As used in the figure, "N" refers to natamycin; "crude lipo" refers to the crude lipopeptide extract; "I" refers to the semi-purified iturin-type compounds; "F" refers to the semi-purified fengycin-type compounds; and "S" refers to the purified surfactin-type compounds.

Results, which show synergy between the various combinations, are shown in FIG. 3 and in Table 1. Table 1 shows the synergy calculation using Gowing's equation, as described above.

TABLE 1

| | % of Growth of the Given Compound(s) at 2.23 ppm | | Gowing's equation | | |
|---|---|---|---|---|---|
| Crude Lipo-peptides | Natamycin | Natamycin + Lipopeptide | Exp | Eob | Synergy? |
| 125.94 | 35.38 | 0.96 | 55.44 | 99.04 | Yes |
| Iturin | Natamycin | Natamycin + Iturin | Exp | Eob | Synergy? |
| 110.39 | 35.38 | 9.38 | 60.94 | 90.62 | Yes |
| Fengycin | Natamycin | Natamycin + Fengycin | Exp | Eob | Synergy? |
| 165.04 | 35.38 | 2.15 | 41.6 | 97.85 | Yes |
| Surfactin | Natamycin | Natamycin + Surfactin | Exp | Eob | Synergy? |
| 79.87 | 35.38 | 1.64 | 71.74 | 98.36 | Yes |

Example 5

Synergistic Effect of Semi-Purified and Purified Iturins, Fengycins, and Surfactins and Natamycin Against *Geotrichum candidum*

Experiments similar to those described above, using *Geotrichum candidum* as the target pathogen, were conducted with (i) natamycin, (ii) crude extracts of lipopeptides from *Bacillus subtilis* QST713 (obtained as described above in Example 1), (iii) combinations of natamycin and the crude extracts, and (iv) combinations of natamycin and semi-purified and purified lipopeptides (i.e., iturin-type compounds, fengycin-type compounds, and surfactin-type compounds) from *Bacillus subtilis* QST713.

Iturin-type compounds and surfactins were extracted and purified from *B. subtilis* QST713 as explained above. Fengycin-type compounds were extracted in the same manner as that for iturin-type compounds but further purified using low pressure reverse phase chromatography to at least 90% purity.

Final concentration of natamycin in each test well was 2.23 ppm; final concentration of the crude lipopeptide extract in each well was 2.23 ppm; final concentration of each semi-purified or purified lipopeptide extract of iturin-type compounds, surfactins or fengycin-type compounds in each well was 2.23 ppm. Thus, the weight to weight ratio of each component in the wells containing combinations was 1:1.

Figure 4:
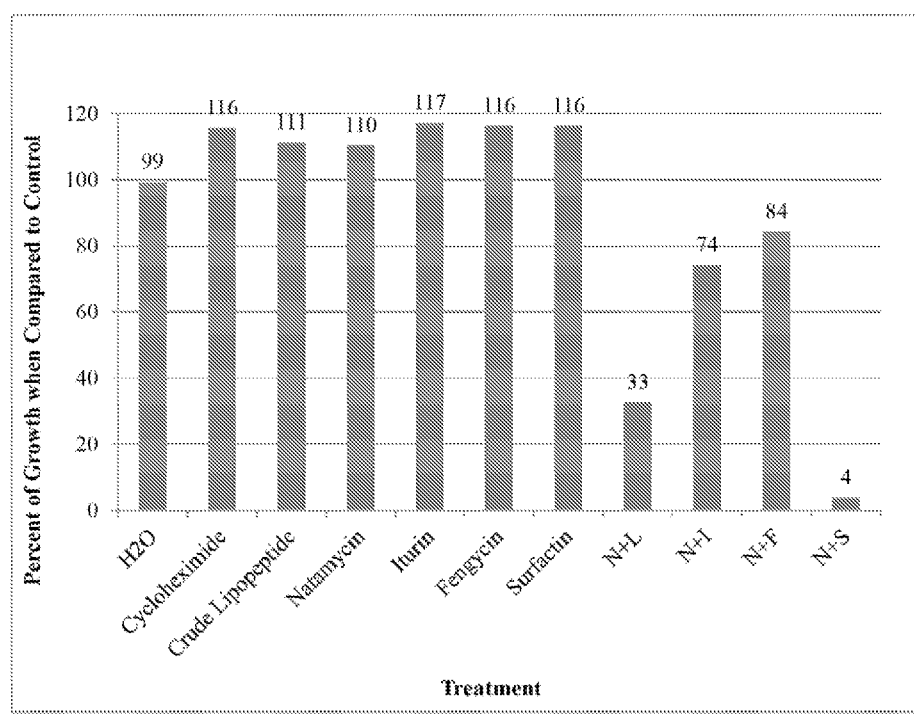
FIG. 4 shows percent growth of *Geotrichum candidum* compared to a negative control in the presence of (i) natamycin, (ii) a crude lipopeptide extract, (iii) various semi-purified or purified lipopeptides, (iv) combinations of natamycin and a crude lipopeptide extract, and (v) combinations of natamycin and each semi-purified or purified lipopeptide. As used in the figure, "N" refers to natamycin; "L" refers to the crude lipopeptide extract; "I" refers to the semi-purified iturin-type compounds; "F" refers to the semi-purified fengycin-type compounds; and "S" refers to the purified surfactin-type compounds.

Results showing synergy between various combinations are described in FIG. 4 and Table 2.

TABLE 2

| | % of Growth of the Given Compound(s) at 2.23 ppm | | Gowing's equation | | |
|---|---|---|---|---|---|
| Crude Lipo-peptides | Natamycin | Natamycin + Lipopeptide | Exp | Eob | Synergy? |
| 111.3 | 110.4 | 32.7 | −22.9 | 67.3 | Yes |
| Iturin | Natamycin | Natamycin + Iturin | Exp | Eob | Synergy? |
| 117.3 | 110.4 | 74.2 | −29.5 | 25.8 | Yes |
| Fengycin | Natamycin | Natamycin + Fengycin | Exp | Eob | Synergy? |
| 116.4 | 110.4 | 84.3 | −28.4 | 15.7 | Yes |
| Surfactin | Natamycin | Natamycin + Surfactin | Exp | Eob | Synergy? |
| 116.4 | 110.4 | 3.8 | −28.4 | 96.2 | Yes |

Example 6

Synergistic Effect of Semi-Purified and Purified Iturins, Fengycins, and Surfactins and Nystatin Against *Geotrichum candidum*

Experiments similar to those described above, using *Geotrichum candidum* as the target pathogen, were conducted with (i) nystatin (another example of a polyene fungicide), (ii) crude extracts of lipopeptides from *Bacillus subtilis* QST713 (obtained as described above in Example 1), (iii) combinations of nystatin and the crude extracts, and (iv) combinations of nystatin and semi-purified and purified lipopeptides (i.e., iturins, fengycins, and surfactins) from *Bacillus subtilis* QST713.

Iturin-type compounds, surfactin-type compounds, and fengycin-type compounds were extracted and purified from *B. subtilis* QST713 as explained above. Final concentration of nystatin in each test well was 1.12 ppm; final concentration of the crude lipopeptide extract in each well was 1.12 ppm; final concentration of each semi-purified or purified lipopeptide extract of iturin-type compounds, surfactins or fengycin-type compounds in each well was 1.12 ppm. Thus, the weight to weight ratio of each component in the wells containing combinations was 1:1.

Figure 5:
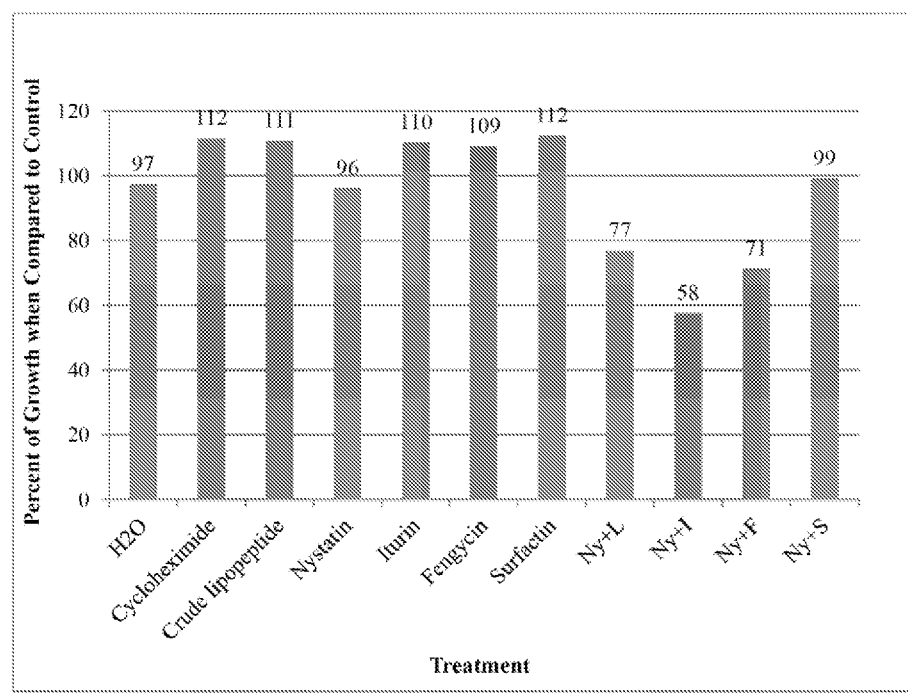
FIG. 5 shows percent growth of *Geotrichum candidum* compared to a negative control in the presence of (i) nystatin, (ii) a crude lipopeptide extract, (iii) various semi-purified or purified lipopeptides, (iv) combinations of nystatin and a crude lipopeptide extract, and (v) combinations of nystatin and each semi-purified or purified lipopeptide. As used in the figure, "Ny" refers to nystatin; "L" refers to the crude lipopeptide extract; "I" refers to the semi-purified iturin-type compounds; "F" refers to the semi-purified fengycin-type compounds; and "S" refers to the purified surfactin-type compounds.

Results showing synergy between various combinations are described in FIG. 5 and Table 3. Applicants note that synergy was not experienced between surfactin and nystatin at the concentrations used in this experiment. It is expected that if final concentrations were varied synergy would result. See comments on a similar situation at the end of Example 9.

TABLE 3

| | % of Growth of the Given Compound(s) at 1.12 ppm | | | Gowing's equation | | |
|---|---|---|---|---|---|---|
| Crude Lipopeptides | Nystatin | Nystatin + Lipopeptide | Exp | Eob | Synergy? |
| 110.8 | 96.2 | 76.9 | −6.6 | 23.1 | Yes |
| Iturin | Nystatin | Nystatin + Iturin | Exp | Eob | Synergy? |
| 110.4 | 96.2 | 57.5 | −6.2 | 42.5 | Yes |
| Fengycin | Nystatin | Nystatin + Fengycin | Exp | Eob | Synergy? |
| 109.3 | 96.2 | 71.4 | −5.1 | 28.6 | Yes |
| Surfactin | Nystatin | Nystatin + Surfactin | Exp | Eob | Synergy? |
| 112.5 | 96.2 | 99.2 | | | No |

Example 7

Synergistic Effect of Semi-Purified and Purified Iturins, Fengycins, and Surfactins and Natamycin Against *Geotrichum citri-aurantii*

Experiments similar to those described above, using *Geotrichum citri-aurantii* as the target pathogen, were conducted with (i) natamycin, (ii) crude extracts of lipopeptides from *Bacillus subtilis* QST713 (obtained as described above in Example 1), (iii) combinations of natamycin and the crude extracts, and (iv) combinations of natamycin and semi-purified and purified lipopeptides (i.e., iturin-type compounds, fengycin-type compounds, and surfactin-type compounds) from *Bacillus subtilis* QST713.

Iturin-type compounds, surfactins, and fengycin-type compounds were extracted and purified from *B. subtilis* QST713 as explained above. Final concentration of natamycin in each test well was 2.23 ppm; final concentration of the crude lipopeptide extract in each well was 2.23 ppm; final concentration of each semi-purified or purified lipopeptide extract of iturin-type compounds, surfactin or fengycin-type compounds in each well was 2.23 ppm. Thus, the weight to weight ratio of each component in the wells containing combinations was 1:1.

Figure 6:
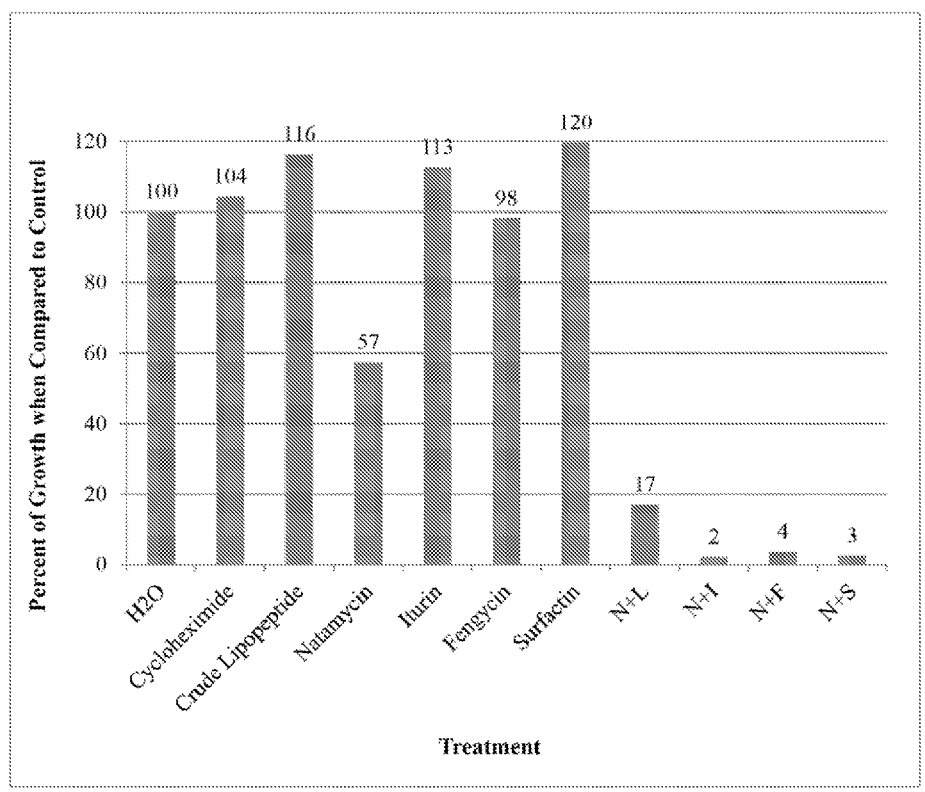
FIG. 6 shows percent growth of *Geotrichum citri-aurantii* compared to a negative control in the presence of (i) natamycin, (ii) a crude lipopeptide extract, (iii) various semi-purified or purified lipopeptides, (iv) combinations of natamycin and a crude lipopeptide extract; and (v) combinations of natamycin and each semi-purified or purified lipopeptide. As used in the figure, "N" refers to natamycin; "L" refers to the crude lipopeptide extract; "I" refers to the semi-purified iturin-type compounds; "F" refers to the semi-purified fengycin-type compounds; and "S" refers to the purified surfactin-type compounds.

Results showing synergy between various combinations are described in FIG. 6 and Table 4.

TABLE 4

| | % of Growth of the Given Compound(s) at 2.23 ppm | | | Gowing's equation | | |
|---|---|---|---|---|---|---|
| Crude Lipo-peptides | Natamycin | Natamycin + Lipopeptide | Exp | Eob | Synergy? |
| 116.3 | 57.4 | 17 | 33.2 | 82 | Yes |
| Iturin | Natamycin | Natamycin + Iturin | Exp | Eob | Synergy? |
| 112.6 | 57.4 | 2.2 | 35.4 | 97.8 | Yes |
| Fengycin | Natamycin | Natamycin + Fengycin | Exp | Eob | Synergy? |
| 98.1 | 57.4 | 3.7 | 43.7 | 96.3 | Yes |
| Surfactin | Natamycin | Natamycin + Surfactin | Exp | Eob | Synergy? |
| 119.6 | 57.4 | 2.6 | 31.3 | 97.4 | Yes |

Example 8

Synergistic Effect of Semi-Purified and Purified Iturins, Fengycins, and Surfactins and Nystatin Against *Geotrichum citri-aurantii*

Experiments similar to those described above, using *Geotrichum citri-aurantii* as the target pathogen, were conducted with (i) nystatin (another example of a polyene fungicide), (ii) crude extracts of lipopeptides from *Bacillus subtilis* QST713 (obtained as described above in Example 1), (iii) combinations of nystatin and the crude extracts, and (iv) combinations of nystatin and semi-purified and purified lipopeptides (i.e., iturin-type compounds, fengycin-type compounds, and surfactin-type compounds) from *Bacillus subtilis* QST713.

Iturin-type compounds, surfactins, and fengycin-type compounds were extracted and purified from *B. subtilis* QST713 as explained above. Final concentration of nystatin in each test well was 2.23 ppm; final concentration of the crude lipopeptide extract in each well was 2.23 ppm; final concentration of each semi-purified or purified lipopeptide extract of iturin-type compounds, surfactin or fengycin-type compounds in each well was 2.23 ppm. Thus, the weight to weight ratio of each component in the wells containing combinations was 1:1.

Figure 7:
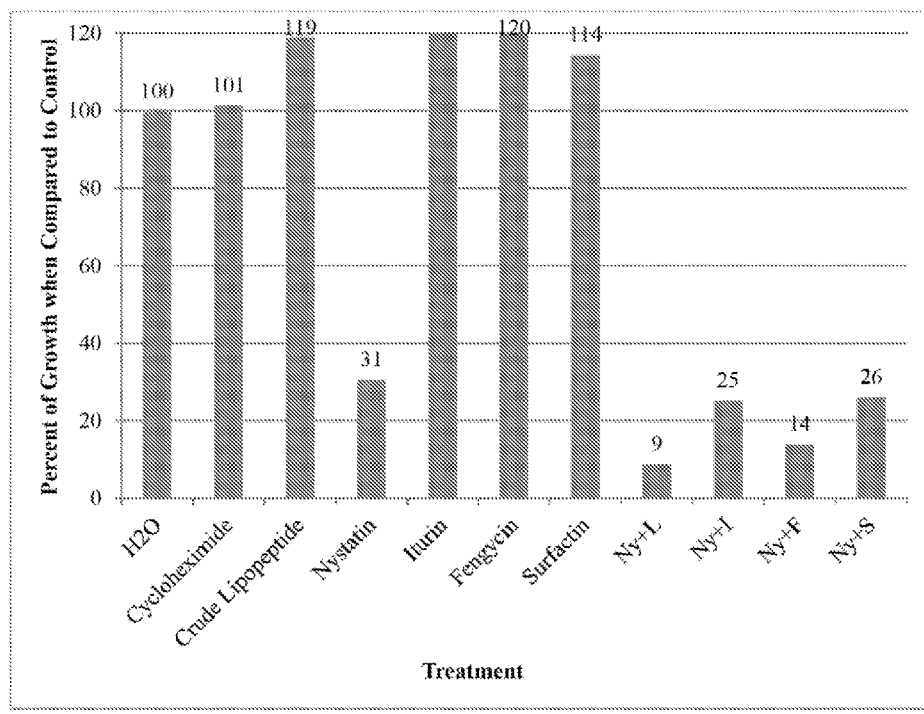
FIG. 7 shows percent growth of *Geotrichum citri-aurantii* compared to a negative control in the presence of (i) nystatin, (ii) a crude lipopeptide extract, (iii) various semi-purified or purified lipopeptides, (iv) combinations of nystatin and a crude lipopeptide extract, and (v) combinations of nystatin and each semi-purified or purified lipopeptide. As used in the figure, "Ny" refers to nystatin; "L" refers to the crude lipopeptide extract; "I" refers to the semi-purified iturin-type compounds; "F" refers to the semi-purified fengycin-type compounds; and "S" refers to the purified surfactin-type compounds.

Results showing synergy between various combinations are shown in FIG. 7 and Table 5.

TABLE 5

| | % of Growth of the Given Compound(s) at 2.23 ppm | | | Gowing's equation | | |
|---|---|---|---|---|---|---|
| Crude Lipopeptides | Nystatin | Nystatin + Lipopeptide | Exp | Eob | Synergy? |
| 118.9 | 30.5 | 8.8 | 63.7 | 91.2 | Yes |
| Iturin | Nystatin | Nystatin + Iturin | Exp | Eob | Synergy? |
| 121.3 | 30.5 | 25.1 | 63 | 74.9 | Yes |
| Fengycin | Nystatin | Nystatin + Fengycin | Exp | Eob | Synergy? |
| 119.8 | 30.5 | 13.9 | 63.4 | 86.1 | Yes |
| Surfactin | Nystatin | Nystatin + Surfactin | Exp | Eob | Synergy? |
| 114.3 | 30.5 | 26 | 65.1 | 74 | Yes |

Example 9

Synergistic Effect of Semi-Purified and Purified Iturins, Fengycins, and Surfactins and Natamycin Against *Saccharomyces cerevisiae*

Experiments similar to those described above, using *Saccharomyces cerevisiae* as the target pathogen, were conducted with (i) natamycin, (ii) crude extracts of lipopeptides from *Bacillus subtilis* QST713 (obtained as described above in Example 1), (iii) combinations of natamycin and the crude extracts, and (iv) combinations of natamycin and semi-purified and purified lipopeptides (i.e., iturin-type compounds, fengycin-type compounds, and surfactin-type compounds) from *Bacillus subtilis* QST713.

As before, liquid fungal growth assays were performed in 96-well plates to determine whether the combination of lipopeptides and natamycin is synergistic in inhibiting fungal growth. Each well of the plate had three separate additions.

First, yeast peptone dextrose media (YPD) was used. Then, 25 μL of each sample (whether lipopeptide, natamycin, or combination of the two from dilution plate) was added. Finally, 50 μL of yeast inoculum or 50 μL of DI H₂O was added (the latter option is used when constructing the blank). Yeast inoculum was prepared by inoculating a single colony in 5 mL YPD and incubated at 30° C. overnight with shaking. In the morning, 200 μL of the overnight inoculum was subcultured into 5 mL YPD and incubated at 30° C. shaking for 4 to 5 hours. This was diluted to an optical density of 0.015. After all three additions, the plates were then covered with lids and incubated at 30° C. overnight to be analyzed the next day.

Iturin-type compounds, surfactins, and fengycin-type compounds were extracted and purified from *B. subtilis* QST713 as explained above. Final concentration of natamycin in each test well was 1.12 ppm; final concentration of the crude lipopeptide extract in each well was 1.12 ppm; final concentration of each semi-purified or purified lipopeptide extract of iturin-type compounds, surfactin or fengycin-type compounds in each well was 1.12 ppm. Thus, the weight to weight ratio of each component in the wells containing combinations was 1:1.

Figure 8:
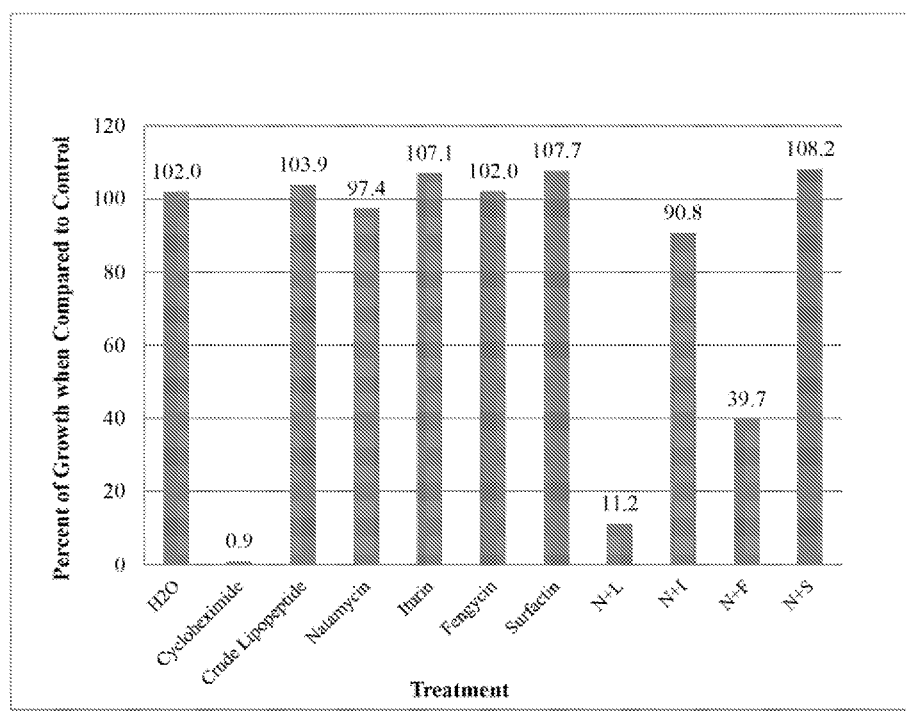
FIG. 8 shows percent growth of *Saccharomyces cerevisiae* compared to a negative control in the presence of (i) natamycin, (ii) a crude lipopeptide extract, (iii) various semi-purified or purified lipopeptides, (iv) combinations of natamycin and a crude lipopeptide extract, and (v) combinations of natamycin and each semi-purified or purified lipopeptide. As used in the figure, "N" refers to natamycin; "L" refers to the crude lipopeptide extract; "I" refers to the semi-purified iturin-type compounds; "F" refers to the semi-purified fengycin-type compounds; and "S" refers to the purified surfactin-type compounds.

Results showing synergy between various combinations are described in FIG. 8 and Table 6. Applicants conducted additional experiments to investigate the lack of synergy between natamycin and surfactin against *S. cerevisiae* at final concentrations of 1.12 ppm each, expecting to find synergy at a higher concentration. Final concentration of surfactin was increased while final concentration of natamycin was held at 1.12 ppm. As expected, synergy was experienced with a higher concentration of surfactin; namely, 17.86 ppm.

TABLE 6

| Crude Lipopeptides | Natamycin | Natamycin + Lipopeptide | Exp | Eob | Synergy? |
|---|---|---|---|---|---|
| % of Growth of the Given Compound(s) at 1.12 ppm | | | Gowing's equation | | |
| 103.9 | 97.4 | 11.2 | −1.3 | 88.8 | Yes |
| Iturin | Natamycin | Natamycin + Iturin | Exp | Eob | Synergy? |
| 107.1 | 97.4 | 90.8 | −4.4 | 9.2 | Yes |
| Fengycin | Natamycin | Natamycin + Fengycin | Exp | Eob | Synergy? |
| 102 | 97.4 | 39.7 | 0.6 | 60.3 | Yes |
| Surfactin | Natamycin | Natamycin + Surfactin | Exp | Eob | Synergy? |
| 107.7 | 97.4 | 108.2 | | | No |

Example 10

Synergistic Effect of Semi-Purified and Purified Iturins, Fengycins, and Surfactins and Nystatin Against *Saccharomyces cerevisiae*

Experiments similar to that described above, using *Saccharomyces cerevisiae* as the target pathogen, were conducted with (i) nystatin, (ii) crude extracts of lipopeptides from *Bacillus subtilis* QST713 (obtained as described above in Example 1), (iii) combinations of nystatin and the crude extracts, and (iv) combinations of nystatin and semi-purified and purified lipopeptides (i.e., iturin-type compounds, fengycin-type compounds, and surfactin-type compounds) from *Bacillus subtilis* QST713.

Iturin-type compounds, surfactins, and fengycin-type compounds were extracted and purified from *B. subtilis* QST713 as explained above. Final concentration of natamycin in each test well was 0.56 ppm; final concentration of the crude lipopeptide extract in each well was 0.56 ppm; final concentration of each semi-purified or purified lipopeptide extract of iturin-type compounds, surfactins or fengycin-type compounds in each well was 0.56 ppm. Thus, the weight to weight ratio of each component in the wells containing combinations was 1:1.

Figure 9:
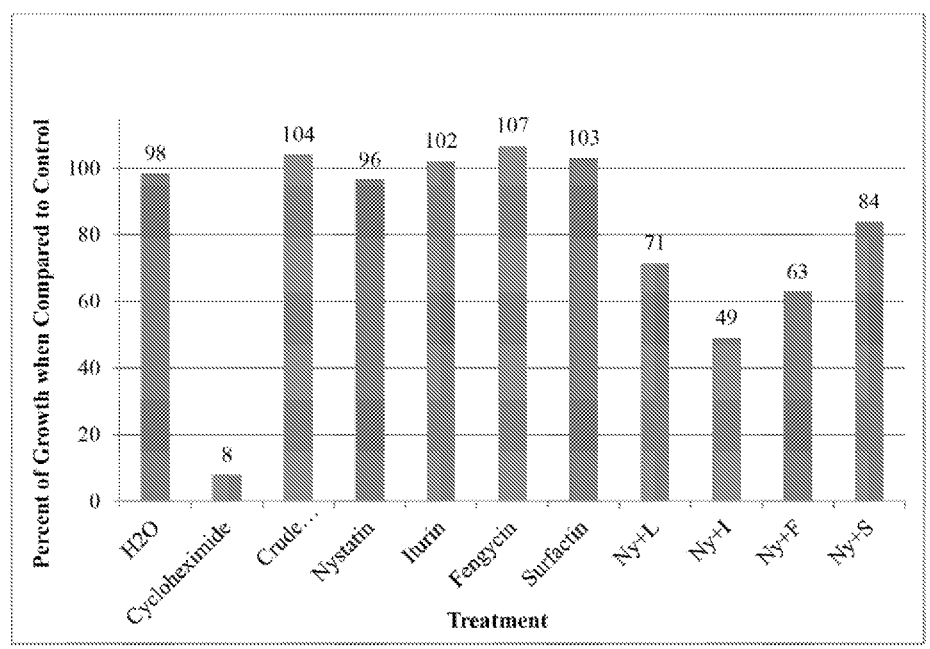
FIG. 9 shows percent growth of *Saccharomyces cerevisiae* compared to a negative control in the presence of (i) nystatin, (ii) a crude lipopeptide extract, (iii) various semi-purified or purified lipopeptides, (iv) combinations of nystatin and a crude lipopeptide extract, and (v) combinations of nystatin and each semi-purified or purified lipopeptide. As used in the figure, "Ny" refers to nystatin; "L" refers to the crude lipopeptide extract; "I" refers to the semi-purified iturin-type compounds; "F" refers to the semi-purified fengycin-type compounds; and "S" refers to the purified surfactin-type compounds.

Results showing synergy between various combinations are described in FIG. 9 and Table 7.

TABLE 7

| Crude Lipopeptides | Nystatin | Nystatin + Lipopeptide | Exp | Eob | Synergy? |
|---|---|---|---|---|---|
| % of Growth of the Given Compound(s) at 0.56 ppm | | | Gowing's equation | | |
| 104 | 96.5 | 71.4 | −0.35 | 28.6 | Yes |
| Iturin | Nystatin | Nystatin + Iturin | Exp | Eob | Synergy? |
| 102.1 | 96.5 | 49 | 1.5 | 51 | Yes |
| Fengycin | Nystatin | Nystatin + Fengycin | Exp | Eob | Synergy? |
| 106.7 | 96.5 | 62.8 | −2.9 | 37.2 | Yes |
| Surfactin | Nystatin | Nystatin + Surfactin | Exp | Eob | Synergy? |
| 102.9 | 96.5 | 83.9 | 0.7 | 16.1 | Yes |

Example 11

Synergy Effect of Natamycin and Crude Extract of Lipopeptides Against *Penicillium expansum* at Different Weight to Weight Ratios Studies were conducted to determine whether synergy was observed with various weight to weight ratios of natamycin to crude extract of lipopeptides. Lipopeptides were extracted from *Bacillus subtilis* QST713 as described in Example 1, above. Efficacy of various combinations were tested against *Penicillium expansum* using the multi-well plate assay described in Example 3. Weight to weight ratios of natamycin to the crude lipopeptide extract were varied from 1:500 to 500:1 and synergy observed in all cases, as summarized in Table 8. Concentrations in Table 8 represent final concentration of each component per well.

TABLE 8

| Concentration of Natamycin (ppm) | Concentration of Lipopeptides (ppm) | Weight to Weight Ratio | Synergy |
|---|---|---|---|
| 1.12 | 1.12 | 1:1 | Yes |
| 1.12 | 0.224 | 5:1 | Yes |
| 1.12 | 0.00224 | 500:1 | Yes |
| 0.08 | 0.08 | 1:1 | Yes |
| 0.016 | 0.08 | 1:5 | Yes |
| 0.0008 | 0.08 | 1:100 | Yes |
| 0.032 | 0.16 | 1:5 | Yes |
| 0.16 | 0.16 | 1:1 | Yes |
| 0.016 | 0.16 | 1:10 | Yes |
| 0.0016 | 0.16 | 1:100 | Yes |

TABLE 8-continued

| Concentration of Natamycin (ppm) | Concentration of Lipopeptides (ppm) | Weight to Weight Ratio | Synergy |
|---|---|---|---|
| 0.00032 | 0.16 | 1:500 | Yes |
| 0.224 | 1.12 | 1:5 | Yes |
| 0.0112 | 1.12 | 1:100 | Yes |

We claim:

1. A composition comprising a synergistic fungicidal combination of a polyene fungicide and at least one lipopeptide, wherein the polyene fungicide is natamycin and the at least one lipopeptide comprises one or more fengycin-type compounds and one or more iturin-type compounds and wherein the weight to weight ratio of the polyene fungicide and the at least one lipopeptide is about 1:1.

2. The composition of Claim 1 further comprising one or more surfactin-type compounds.

3. The composition of claim 1 wherein the at least one lipopeptide is part of or an extract of a fungicidal lipopeptide-containing fermentation product.

4. The composition of claim 3 wherein the lipopeptide-containing fermentation product is from a *Bacillus* species bacteria.

5. The composition of claim 4 wherein the *Bacillus* species bacteria is selected from the group consisting of *Bacillus subtilis* and *Bacillus amyloliquefaciens*.

6. The composition of claim 4 wherein the *Bacillus subtilis* is selected from the group consisting of *Bacillus subtilis* QST713 and its variants.

7. A method for controlling fungal phytopathogens comprising applying to a plant, root, seed or soil surrounding the plant an effective amount of a composition comprising a synergistic fungicidal combination of a polyene fungicide and at least one lipopeptide, wherein the polyene fungicide is natamycin and the at least one lipopeptide comprises one or more fengycin-type compounds and one or more iturin-type compounds and wherein the weight to weight ratio of the polyene fungicide and the at least one lipopeptide is about 1:1.

8. The method of claim 7 wherein the at least one lipopeptide further comprises one or more surfactin-type compounds.

* * * * *